United States Patent
Pinto et al.

(10) Patent No.: US 7,404,962 B1
(45) Date of Patent: Jul. 29, 2008

(54) COMBINATION KIT USED IN THE TREATMENT OF MALARIA

(75) Inventors: Francis Joseph Pinto, Mumbai (IN);
Swati Ajay Piramal, Mumbai (IN);
Ram Pratap, Lucknow (IN); Amiya
Prasad Bhaduri, Lucknow (IN); Harsh
Pati Thapliyal, Lucknow (IN); Sunil
Kumar Puri, Lucknow (IN); Guru
Prasad Dutta, Lucknow (IN); Anil
Kumar Dwivedi, Lucknow (IN);
Satyawan Singh, Lucknow (IN);
Pratima Srivastava, Lucknow (IN);
Vikash Chandra Pandey, Lucknow
(IN); Sudhir Srivastava, Lucknow (IN);
Shio Kumar Singh, Lucknow (IN);
Ram Chandra Gupta, Lucknow (IN);
Jagdishwar Sahai Srivastava, Lucknow
(IN); Omkar Prasad Asthana, Lucknow
(IN)

(73) Assignees: Nicholas Piramal India Limited,
Mumbai (IN); **Council of Scientific and
Industrial Research**, New Delhi (IN)

( * ) Notice: Subject to any disclaimer, the term of this
patent is extended or adjusted under 35
U.S.C. 154(b) by 711 days.

(21) Appl. No.: 10/296,215

(22) PCT Filed: Aug. 30, 2000

(86) PCT No.: PCT/IN00/00081

§ 371 (c)(1),
(2), (4) Date: Jun. 4, 2003

(87) PCT Pub. No.: WO01/91535

PCT Pub. Date: Dec. 6, 2001

(30) Foreign Application Priority Data

May 31, 2000 (IN) .......................... 501/MUM/2000

(51) Int. Cl.
*A61K 39/015* (2006.01)
*C07D 215/38* (2006.01)

(52) U.S. Cl. .................. 424/268.1; 424/272.1; 546/171

(58) Field of Classification Search .................. 514/308,
514/311, 312, 314, 895; 424/268.1, 272.1;
546/171
See application file for complete search history.

(56) References Cited

U.S. PATENT DOCUMENTS 4,431,807 A * 2/1984 Strube et al. ................. 546/171
5,373,005 A * 12/1994 McCann et al. ............. 514/217

OTHER PUBLICATIONS

J.S. Lunn et al., "Antibody production in Plasmodium vivax infections suppressed by weekly doses of chloroquine", American Journal of Tropical Medicine and Hygiene, (Sep. 1965), 14(5), pp. 697-699.*
K. Kar et al., "Pharmacology of Compound CDRI 80/53; A Potential New Anti-Relapde Antimalarial Agent", Indian Journal of Parasitology, (1988), pp. 259-262.*
Paliwal, Jyoti Kumar and Ram Chandra Gupta. "A Rapid and Sensitive High Performance Liquid Chromatographic Assay of the New Antimalarial Compound 80/53 in Serum with a Novel Sample Cleanup Method and its Pharmacokinetics in Rabbits. Journal of Pharmaceutical and Biomedical Analysis." vol. 17, pp. 775-783 (1998).*

* cited by examiner

*Primary Examiner*—Raymond J. Henley, III
*Assistant Examiner*—Alicia Hughes
(74) *Attorney, Agent, or Firm*—Westerman, Hattori, Daniels & Adrian, LLP.

(57) ABSTRACT

A combination kit for the treatment of malaria caused by *Plasmodium vivax* (*P. vivax*) having individual doses of an anti-malarial agent, 3-[1-[[4-[(6-methoxy-8-quinolinyl) amino]pentyl]amino]ethylidene]-dihydro-2(3H)-furanone (I) in the form of capsules; individual doses of the antimalarial agent, chloroquine in the form of tablets; and instruction material for the administration of the two anti-malarial drugs. The combination kit is particularly suited for a 6 days treatment regimen where the treatment is rendered by five tablets containing 500 mg of chloroquine phosphate (equivalent to 300 mg base), three to be taken on day one and one each on days two and three; and five capsules containing 25 mg of 3-[1-[[4-[(6-methoxy-8-quinolinyl)amino]pentyl]amino] ethylidene]-dihydro-2(3H)-furanone (I), one each to be taken on days two to six.

1 Claim, No Drawings

US 7,404,962 B1

COMBINATION KIT USED IN THE TREATMENT OF MALARIA

FIELD OF INVENTION

The present invention relates to a combination kit for use in the treatment of malaria and a method for producing such a kit. Particularly, the invention relates to a combination kit comprising anti-malarial agents, 3-[1-[[4-[(6-methoxy-8-quinolinyl)amino]pentyl]amino]-ethylidene]-dihydro-2(3H) furanone and chloroquine. More particularly, the present invention relates to the use of the combination kit containing an anti-malarial agent, 3-[1-[[4-[(6-methoxy-8-quinolinyl) amino]pentyl]-amino]ethylidene]-dihydro-2(3H)-furanone and chloroquine against relapsing malaria caused by *Plasmodium vivax* for better patient compliance. The present invention further relates to a method for the treatment of malaria caused by *P. vivax*.

BACKGROUND OF THE INVENTION

Malaria, caused by a parasitic protozoan called Plasmodium, is one of the most serious and complex tropical parasitic diseases. Generally human malaria is caused by four species of malarial parasites which are *Plasmodium falciparum, Plasmodium vivax, Plasmodium ovale* and *Plasmodium malariae*. Of these *P. falciparum* and *P. vivax* are most widespread and cause most of the mortality and morbidity associated with these types of infections.

It is known that the material parasites undergo complex life cycle in humans, which is initiated through the bite of an infected female Anopheles mosquito. When the mosquito bites a host, some of the sporozoites are injected into the bloodstream of the host and through the circulation they reach the liver where they multiply and liberate merozoites into the bloodstream which then invade the erythrocytes. In case of infections caused by *P. vivax*, most of the time the parasites remain dormant in the liver which stage is termed hypnozoites. Hypnozoites are reactivated and reinitiate blood stage parasitemias causing relapse. It has often been observed that people infected with *P. vivax* do not experience any symptoms for a very lone period after their initial illness but become symptomatic after certain period (Korean J. Intern Med, 1999 Jul; 14(2): 86-9).

A number of drugs ranging from those of natural origin to synthetic ones have been developed for the treatment of malaria. Quinine and artemisinin are the commonly know drugs of natural origin, which are mostly used for the treatment of malaria. A number of synthetic anti-malarial drugs such as chloroquine, mefloquine, primaquine, halofantrine, amodiaquine, proguanil, maloprim are known in the literature. Of all the synthetic anti-malarial agents chloroquine has been the most widely prescribed drug for the treatment of malaria of all the types, for more than last 60 years.

Chloroquine has been the effective treatment so far for the *P. vivax* malarial infections, however, some strains of *P. vivax* have shown resistance to this well known drug (*Ann. Trop. Med. Parasitol.*, 1999 Apr; 93(3): 225-230). In recent years drug resistant malaria has become one of the most serious problems in malaria control. Drug resistance necessitates the use of drugs which are more expensive and may have dangerous side effects. To overcome the problems associated with drug resistance, treatments comprising combinations of anti-malarial agents are on the rise. A number of anti-malarial combinations are already known in the malarial chemotherapy. For example, a combination of amodiaquine and tetracycline, a combination of sulfadoxine and pyrimethamine known as fansidar, are known therapies for the treatment of *P. falciparum*. Also fansimef, a combination of mefloquine with sulfadoxine and pyrimethamine is used against multidrug resistant strains of *P. falciparum*.

U.S. Pat. No. 5,998,449 describes a method for the treatment of malaria wherein combination of atovaquone and proguanil is used for the treatment of malaria. In U.S. Pat. No. 5,834,505, combination of fenozan with another anti-malarial agent selected from artemisinin, sodium artesunate, chloroquine, mefloquine is described for the prophylactic and curative treatment of malaria.

All the aforementioned anti-malarial combinations reported heretofore are generally used for the treatment of *P. falciparum*. None of the standard anti-malarial combination treatment regimens have been found to be favourable for the treatment of *P. vivax* malaria which is the most relapsing type of malaria. For a very long time chloroquine was used for the treatment of infections caused by *P. vivax*, however, chloroquine eradicates only the asexual erythrocytic stages of *P. vivax* and does not eliminate the hypnozoites. Until recently primaquine has been the drug of choice for the treatment of malarial relapse. Generally the standard therapy for the *P. vivax* malarial infection comprises of a sequential chloroquine-primaquine combination treatment regimen wherein primaquine is administered for 14 days following the 3 days course of chloroquine. WHO (World Health Organisation) also recommends a 14 days primaquine treatment for *P. vivax* malarial infection. A shorter duration of chloroquine-primaquine treatment regimen was also tried out wherein primaquine was administered only for 5 days following the chloroquine course. However, the outcome of the treatment was not encouraging, since the percentage relapse was more than the standard 14 days primaquine treatment regimen (Trans. R. Soc. Trop. Med. Hyg., 93(6), 641-643). Also primaquine is known to cause hemolytic anemia in persons deficient in the enzyme glucose-6-phosphate dehydrogenase (G6PD) (Pharmacol Rev. 21: 73-103 (1969); Rev. Cubana Med trop, 1997; 49 (2):136-8). Moreover, methemoglobin toxicity is another predictable does-related adverse effect associated with primaquine. Needless to say that in the case of sequential combination therapy the patient may not complete the course once the symptoms of malaria are diminished, hence this may increase the chances of relapse. Thus, the chloroquine-primaquine treatment regimen is not safe with respect to toxicity of primaquine and has a further limitation from the standpoint of patient compliance due to longer duration of treatment.

Another anti-relapse agent namely tafenoquine is disclosed in U.S. Pat. No. 4,617,394. Though more effective than primaquine, the drug was found to cause methemoglobin toxicity almost three times more than that of primaquine (Fundam. Appl. Toxicol. 1988, 10(2), 270-275), hence has drawbacks in terms of safety.

The compound, 3-[1-[[4-[(6-methoxy-8-quinolinyl) amino]pentyl]amino]-ethylidene]-dihydro-2(3H)furanone is a derivative of primaquine. It was described in Indian Patent Specification No. 158111 as 6-methoxy-8-(4-N-(3'-aceto-4', 5'-dihydro-2-furanylamino)-1-methylbutylamino)quinoline, the structure of which was revised to that represented by the following formula I. As per the revised structure, the compound is named 3-[1-[[4-[(6-methoxy-8-quinolinyl)amino] pentyl]amino]ethylidene]-dihydro-2(3H)-furanone (hereinafter referred to as compound I). The revised structure is described in WHO Drug Information Vol. 13, No. 4, pg. 268 (1999).

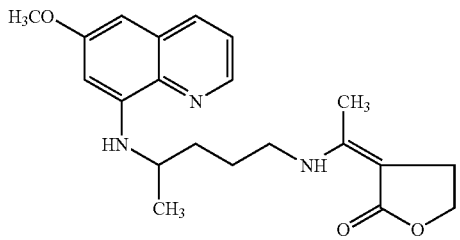

The compound of formula (I) has been found to be safer and less toxic than the present compound primaquine (Am. J. Trop. Med. Hyg, 1989 Dec.; 41(6): 635-637). Its anti-relapse activity has been found to be comparable to primaquine.

Over the years primaquine was the only drug used for the radical cure of malaria caused by *P. vivax*. Primaquine is associated with a number of severe adverse effects, therefore there is a need to develop agents which are more effective and/or less toxic than primaquine. The compound I has been found to exhibit anti-relapse activity comparable to Primaquine (Am. J. Trop. Med. Hyg., 41(6): 633-637 (1989)). However, this compound has been shown to cause less methemoglobin formation (Am. J. Trop Hyg., 41(6): 638-642 (1989)) and also has less effect on anti-oxidant defense enzymes than primaquine (Biochem Pharmacol. 46(10): 1859-1860 (1993)). Thus, this primaquine derivative (I) is found to be less toxic as compared to the parent drug, primaquine.

Therefore, there is a longfelt need for a more practical, effective, patient compliant and safe remedy for the radical cure of *P. vivax* malarial infection.

The inventors have found that the longfelt need may be fulfilled by providing a treatment regimen consisting of regulated use of chloroquine and 3-[1-[[4-[(6-methoxy-8-quinolinyl)amino]pentyl]amino]ethylidene]-dihydro-2(3H)furanone of formula I over a period of between 5 to 8 days.

It has also been found that the treatment regimen may be executed most effectively and in a user friendly manner by providing a combination kit which comprises two anti-malarial agents, namely chloroquine and 3-[1-[[4-[(6-methoxy-8-quinolinyl)amino]pentyl]amino]ethylidene]-dihydro-2(3H)furanone and an instruction material containing instructions for the administration of two anti-malarial agents during the period of treatment.

Thus the present invention relates to a combination kit for the treatment of *P. vivax* malaria for a period of between 5 to 8 days which comprises
 a) a predetermined dose of a first anti-malarial agent namely chloroquine;
 b) predetermined dose of second anti-malarial agent namely 3-[1-[[4-[(6-methoxy-8-quinolinyl)amino]pentyl]amino]-ethylidene]-dihydro-2(3H)furanone;
 c) an instruction manual containing instructions for administering the two anti-malarial agents during the treatment period.

The present invention also relates to a method for producing a combination kit for the treatment of *P. vivax* malaria for a period of between 5 to 8 days which comprises:
 a) providing a predetermined dose of a first anti-malarial agent namely chloroquine;
 b) providing a predetermined dose of second anti-malarial agent namely 3-[1-[[4-[(6-methoxy-8-quinolinyl) amino]pentyl]-amino]ethylidene]-dihydro-2(3H)furanone;
 c) providing an instruction manual containing instructions for administering the two anti-malarial agents during the treatment period.

The present invention further relates to a method of treatment of malaria caused by *P. vivax* comprising administering a first anti-malarial agent, chloroquine and a second anti-malarial agent, 3-[1-[[4-[(6-methoxy-8-quinolinyl)amino] pentyl]amino]ethylidene]-dihydro-2(3H)furanone in predetermined doses and in a predetermined sequence for a period of between 5 to 8 days.

DETAILED DESCRIPTION OF THE INVENTION

According to a preferred aspect of the invention there is provided a combination kit for the treatment of malaria caused by *P. vivax* for a period of between 5 to 8 days comprising:
 1. individual doses of the anti-malarial agent, chloroquine in the form of tablets and;
 2. individual doses of the anti-malarial agent, 3-[1-[[4-[(6-methoxy-8-quinolinyl)amino]pentyl]amino]ethylidene]-dihydro-2(3H)-furanone (I) in the form of capsules
 3. instruction material for the administration of the two anti-malarial drugs.

In accordance with a typical embodiment of the invention, there is provided a combination kit for 6 days treatment of malaria caused by *P. vivax* comprising:
 a) five tablets containing 500 mg of chloroquine phosphate (equivalent to 300 mg base).
 b) five capsules containing 25 mg of 3-[1-[[4-[(6-methoxy-8-quinolinyl)amino]pentyl]amino]ethylidene]-dihydro-2(3H)-furanone;
 c) instruction material having directions to administer treatment in the following manner:
  (i) to administer three tablets containing 500 mg of chloroquine phosphate (equivalent to 300 mg base) on day one;
  (ii) to administer one capsule containing 25 mg of compound I concurrently with a tablet containing 500 mg of chloroquine phosphate (equivalent to 300 mg base) from day two to three; and
  (iii) to administer one capsule containing 25 mg of compound I from day four to day six.

In accordance with a further typical embodiment of the invention, there is provided a method for the treatment of malaria caused by *P. vivax* for a period of six days comprising:
 1. administering three tablets containing 500 mg of chloroquine phosphate (equivalent to 300 mg base) on day one;
 2. administering one capsule containing 25 mg of compound I concurrently with a tablet containing 500 mg of chloroquine phosphate (equivalent to 300 mg base) from day two to three; and
 3. administering one capsule containing 25 mg of compound I from day four to day six.

KIT

The kit used in the present invention may be one or more strips in which the anti-malarial agents are packed individually or in combination. The kit may further comprise an enclosure in the form of a small carton or otherwise. The instruction is in the form of printed instructions provided inside the carton. The instructions may also be printed on the carton and/or on the strip or strips themselves. The instructions may be in English and/or in any national or regional language. An illustration of an instruction material for a 6 days treatment regimen is shown in Table 1 below, although other forms of instructions materials are not excluded from the scope of the invention. The combination kit is prepared by packing the strip/strips in a cardboard packaging on which the instructions for the administration of the anti-malarial agents are contained.

TABLE 1

INSTRUCTION MANUAL FOR 6 DAYS TREATMENT OF MALARIA CAUSED BY *Plasmodium vivax*

|  | DAY 1 | DAY 2 | DAY 3 | DAY 4 | DAY 5 | DAY 6 |
|---|---|---|---|---|---|---|
| CHLORO-QUINE TABLET | Start with 2 tablets 1 tablet after 6 hours | 1 tablet + | 1 tablet + | X | X | X |
| CAPSULE OF COMPOUND OF FORMULA (I) | X | 1 capsule | 1 capsule | 1 capsule | 1 capsule | 1 capsule |

The radical curative anti-malarial activity and toxicity of the compound I was evaluated and compared with that caused by primaquine. The curative activity of compound I was evaluated against *P. cynomolgi* (a Plasmodium species which closely resembles the human malarial parasite *P. vivax*), in rhesus monkeys for 7 days and the compound was found to be 100% curative in the dose range of 1.25 mg/kb to 4 mg/kg Also there was no relapse observed up to 100 days after stopping the treatment.

The efficacy of the combination kit of the present invention, containing compound I (25 mg) was clinically evaluated and compared with primaquine (15 mg) used in combination with chloroquine in a group of patients over a one year surveillance study. The overall study confirmed that the combination kit of the present invention can be used effectively in *P. vivax* malarial infection and that the compound I is as effective as primaquine with respect to radical curative activity.

Although equipotent to primaquine, compound I has been found to be safer than primaquine with respect to the toxicity related to methemoglobin formation. In a comparative toxicity study of compound I with primaquine in healthy human volunteers, it was found that the methemoglobin level increased from 2.29% to 3.02% in case of compound I (25 mg daily for 7 days) as against the increase in methemoglobin level from 3.97% to 16.23% in case of primaquine (at 15 mg daily for 7 days). Thus, the methemoglobin toxicity study proves that the compound I is distinctly safer than primaquine.

The invention thus includes the use of this safer anti-relapse agent, compound I with chloroquine in the form of a combination kit for the radical cure of *P. vivax* malaria. According to a typical aspect described above, the total course of treatment wherein compound I is administered concurrently with chloroquine lasts for 6 days only whereas in the chloroquine-primaquine treatment regimen, the total course of the effective treatment is 17 days.

Thus, the novel combination therapy of the present invention comprising the use of compound I in combination with chloroquine has distinct advantages in terms of safety and improved patient compliance due to shorter duration of treatment.

Hence, the use of the combination kit of the present invention containing chloroquine and the compound I becomes a very useful treatment from the standpoint of low toxicity. In addition to this, concurrent administration of the drugs and shorter duration of the treatment may also improve patient compliance.

The chloroquine tablets and capsules of compound I may be obtained commercially or prepared by conventional methods. For instance, the capsules containing compound I may be prepared by first mixing appropriate quantities of compound I along with the excipients lactose, colloidal silicon dioxide and magnesium stearate in an octagonal blender to obtain a powdered mixture and further filling hard gelatine capsule shells with the resulting mixture. The capsules are blister packed using approved PVC film and aluminum foil.

The dosage of the drugs depends on the need of an individual and the dosages described herein are adult doses. However, this invention is not limited to the dosage of the combination regimen described herein and may be varied according to medical advice. Accordingly the specific dosage described in the typical embodiment is only illustrative and non-limiting combination kits for other dosage forms are also included in the scope of this invention.

The term relapse is used herein to indicate that the symptoms of malaria recur.

The invention will now be described in further details with respect to the following non-limiting examples:

EXAMPLE 1

Combination kit consisting of chloroquine tablets and capsules of 3-[1-[[4-[(6-methoxy-8-quinolinyl)amino]pentyl]amino]ethylidene]-dihydro-2-(3H)furanone (I)

A. Each tablet contains 500 mg of chloroquine phosphate equivalent to 300 mg chloroquine base. The tablet containing chloroquine may be prepared by conventional techniques.

B. Each capsule contains 25 mg of 3-[1-[[4-[(6-methoxy-8-quinolinyl)amino]pentyl]amino]ethylidene]-dihydro-2(3H)furanone (I).

The capsule containing compound I may be prepared according to the following formulation by the procedure as described:

| Compound I | 25 mg |
|---|---|
| Lactose | 250 mg |
| Colloidal silicon dioxide | 2 mg |
| Magnesium stearate | 10 mg |

Procedure:

Compound I (25mg), lactose (250 mg), colloidal silicon dioxide (2 mg) are separately sifted through an S. S. screen no. 40 fitted on a vibratory sifter and transferred to a octagonal blender and the contents are mixed for 40-45 minutes. Then magnesium stearate (10 mg) is sifted through a S. S. screen no. 40 fitted on a vibratory sifter and transferred to the octagonal blender. The contents are further mixed for 10-15 minutes. The resulting powdered mixture is then filled in size '2' double locking gelatine capsule shells which are further polished using a capsule polishing machine.

C. The patients may be given the following treatment over a period of six days.
Day 1: Three tables of chloroquine phosphate 500 mg (equivalent to 300 mg base).
Day 2: One tablet of chloroquine phosphate 500 mg (equivalent to 300 mg base) and one capsule containing 25 mg of compound I.

Day 3: One tablet of chloroquine phosphate 500 mg (equivalent to 300 mg base) and one capsule containing 25 mg of compound I.
Day 4: One capsule containing 25 mg of compound I.
Day 5: One capsule containing 25 mg of compound I.
Day 6: One capsule containing 25 mg of compound I.

EXAMPLE 2

Combination regimen of chloroquine and 3-[1-[[4-[(6-methoxy-8-quinolinyl)amino]pentyl]amino]ethylidene]-dihydro-2(3H)furanone(I) tested against *P. cynomolgi* in rhesus monkeys.

The therapeutic effect of the combination regimen consisting of chloroquine and 3-[1-[[4-[(6-methoxy-8-quinolinyl)amino]pentyl]amino]-ethylidene]-4,5-dihydro-2(3H)furanone (I) was tested against *P. cynomolgi* in rhesus monkeys. 3-[1-[[4-[(6-methoxy-8-quinolinyl)-amino]pentyl]amino]ethylidene]-dihydro-2(3H)furanone(I) was administered in the dose level of 4.00 mg/kg (to 3 monkeys), 3.00 mg/kg (to 3 monkeys), 2.50 mg/kg (to 4 monkeys), 2.00 mg/kg (to 3 monkeys) and 1.25 mg/kg (to 9 monkeys) for 7 days. Chloroquine was administered as a companion drug at 5 mg/kg (base) dose. Minimum curative dose of compound I was found 1.25 mg/kg in 9 monkeys. Doses higher than 1.25 mg/kg i.e. 2.0 mg/kg (base), 3.00 mg/kg (base), 2.50 mg/kg (base), and 4.00 mg/kg (base) were also found to be curative in 3 monkeys, 3 monkeys, 4 monkeys and 3 monkeys respectively. After stopping the treatment all the monkeys were observed over a period of 100 days and the blood smears remained negative in all the monkeys.

EXAMPLE 3

Toxicity Study Data

3-[1-[[4-[(6-methoxy-8-quinolinyl)amino]pentyl]amino]ethylidene]-dihydro-2(3H)furanone (I) was evaluated vis-à-vis primaquine for toxicity related to methemoglobin formation in human.

The methemoglobin toxicity of compound I was evaluated vis-à-vis that of primaquine in normal human volunteers. It was found that when the human subjects were administered with 25 mg daily dose of compound I for 7 days the methemoglobin level rose from 2.29% to 3.02% and in case of 15 mg daily dose of primaquine for 7 days the methemoglobin level rose from 3.97% to 16.23%.

It is thus evident from above data that the compound I is safer than primaquine.

The invention claimed is:

1. A method for the treatment of malaria caused by *P. vivax* comprising administration of a first anti-malarial agent, chloroquine phosphate and a second anti-malarial agent having the structural formula

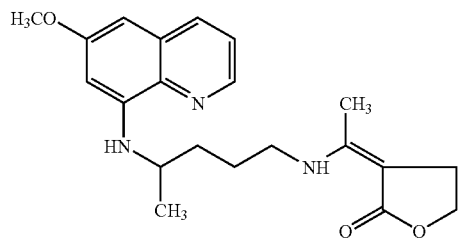

[3-[1-[[4-[(6-methoxy-8-quinolinyl)amino]pentyl]amino]ethylidene]-dihydro-2(3H)-furanone] (compound I)
in predetermined doses and a predetermined sequence over a period of six days, said method comprising:
 a) administering three tablets containing 500 mg each of chloroquine phosphate alone (equivalent to 300 mg chloroquine base) on day one;
 b) administering one capsule containing 25 mg of compound I concurrently with a tablet containing 500 mg of chloroquine phosphate (equivalent to 300 mg chloroquine base) from day two to three; and
 c) administering one capsule containing 25 mg of compound I alone from day four to six.

* * * * *